US 6,569,440 B1

(12) United States Patent
Corma Canos et al.

(10) Patent No.: US 6,569,440 B1
(45) Date of Patent: May 27, 2003

(54) EMITTER OF SEMIOCHEMICAL SUBSTANCES SUPPORTED ON A SEPIOLITE, PREPARATION PROCESS AND APPLICATIONS

(75) Inventors: Avelino Corma Canos, Valencia (ES); Juan Muñoz Pallares, Valencia (ES); Eduardo Primo Yufera, Valencia (ES)

(73) Assignees: Consejo Superior De Investigaciones Cientificas, Madrid (ES); Universidad Politecnica De Valencia, Valencia (ES)

( * ) Notice: Subject to any disclaimer, the term of this patent is extended or adjusted under 35 U.S.C. 154(b) by 0 days.

(21) Appl. No.: 09/508,018

(22) PCT Filed: Jul. 7, 1999

(86) PCT No.: PCT/ES99/00217

§ 371 (c)(1),
(2), (4) Date: Mar. 6, 2000

(87) PCT Pub. No.: WO00/02448

PCT Pub. Date: Jan. 20, 2000

(30) Foreign Application Priority Data

Jul. 8, 1998 (ES) .............................................. 9801473

(51) Int. Cl.[7] .............................................. A01N 25/12
(52) U.S. Cl. ...................... 424/421; 424/405; 424/409; 424/683; 514/770
(58) Field of Search .......................... 424/84, 683, 405, 424/409, 421, 724; 514/770, 771, 762, 763

(56) References Cited

U.S. PATENT DOCUMENTS

| 4,323,556 | A | | 4/1982 | Dal Moro et al. |
| 5,008,478 | A | * | 4/1991 | Bartelt et al. ................. 585/16 |
| 5,035,886 | A | | 7/1991 | Chakrabarti et al. |
| 5,064,820 | A | * | 11/1991 | Fukuto et al. ................. 514/34 |
| 5,633,236 | A | * | 5/1997 | Warren et al. ................. 574/63 |
| 5,958,922 | A | * | 9/1999 | McAuliffe et al. ....... 514/229.2 |

FOREIGN PATENT DOCUMENTS

WO     WO8704591     8/1987

* cited by examiner

Primary Examiner—Neil S. Levy
(74) Attorney, Agent, or Firm—Klauber & Jackson

(57) ABSTRACT

The present invention provides an emitter of semiochemical substances that comprising a support and a semiochemical subsistence adsorbed in the same, is characterized in that said support is a sepiolite and in that the retaining force between said sepiolite and said semiochemical substance is regulated in such a way that a controlled emission kinetics of said semiochemical substance is obtained.

Figure 1:
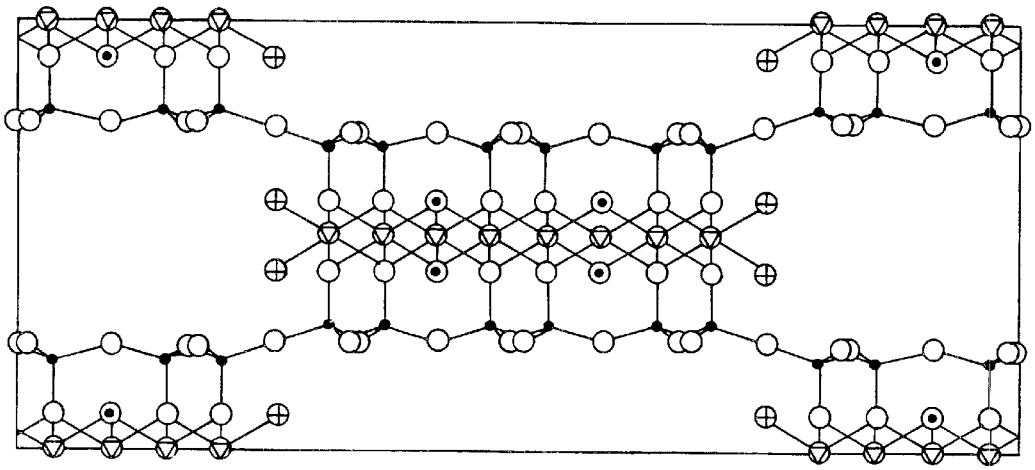

The process for the manufacture of said emitter comprises the operations of modifying a natural sepiolite and of associating it to a semiochemical substance, in such a way that the same is retained with a force such that the emitter has a controlled release kinetics of the substance.

The cited emitter is especially useful in the agricultural sector, for insect plague control in crops.

22 Claims, 3 Drawing Sheets

EMITTER OF SEMIOCHEMICAL SUBSTANCES SUPPORTED ON A SEPIOLITE, PREPARATION PROCESS AND APPLICATIONS

TECHNICAL FIELD OF THE INVENTION

The present invention fits in the agricultural sector and, in particular, in the control of insect plagues detrimental to crops.

More specifically, the present invention provides new emitters of semiochemical substances, with controlled emitting speed, useful for the control of insect plagues in agricultural crops and the process for the preparation thereof.

PRIOR ART OF THE INVENTION

Insect plagues cause a drastic reduction of crops and insecticides are the traditional method to combat them. However, the use of insecticides has problems such as:

- Their toxicity for humans and superior animals, which causes governments to impose more restrictive regulators for the use thereof.
- The lack of selectivity, that converts into the destruction of beneficial insects, or of natural predators of the plague that is to be fought
- The resistance developed by the insects, which makes it necessary to increase more and more the dosage to maintain the effectiveness thereof.

All of these problems oblige insecticide manufacturers to dedicate more and more resources to R+D in order to obtain better products, but the problem continues to exist.

On its part, society demands respect for the environment but at the same time it requires quality of the agricultural food products, which requires the development of new plague control systems based environmental methods.

It is well known that the communication among insects is basically done by means of a specific type of substances, called "semiochemical substances" (or simply "semiochemicals"), that their organisms naturally emit.

The knowledge of said semiochemical substances as well as the knowledge of the information that the same transmit to the insects permits the development of environmental methods in order to control the behavior of the insects.

In accordance with the above, it is possible to transmit a specific message to a specific species of insects, inducing a specific response by means of the artificial emission of synthetic semiochemicals. Hence, for example, if the message is of attraction, the response of the insect will be directed towards the emitter.

Taking advantage of this inducing capacity the behavior of insects, techniques that permit the control thereof have been developed. Hereinafter a summary of the most important ones is going to be made:

- Control, whose purpose is to prevent the occurrence of plagues, to follow their development and to confirm their extinction by means of a count of the captures that are produced in traps provided with an emitter of an attracting semiochemical.
- Sexual confusion, that seeks to prevent the reproduction of insects by means of the emission of amounts of a semiochemical that saturates the receptor organs of the insect preventing it to find members of its same species and of the opposite sex.
- Massive captures, that seek to significantly reduce the insect population, by means of captures, in traps, with an attracting semiochemical. Aside from the attractant, a toxic agent for the insect, a sexual sterilizer, an entomopathogenic microorganism or simply glue where the insect is adhered and dies, may also be placed in the traps.

The low toxicity of semiochemicals, their high specificity (generally, their action is directed towards a single species), the difficult occurrence of resistances and their non-existent polluting impact, represent outstanding advantages in contrast to conventional insecticides.

So that the use of these semiochemical substances is effective it is necessary to have physical supports capable of emitting the semiochemicals in a controlled manner for a sufficient amount of time, in such a way that a concentration in the air capable of cause the desired response in the insect in a continued manner is achieved.

The cited supports must comply with a series of requirements so that their use is effective:

- Provide an adequate emitting speed of the semiochemical.
- Permit prolonged duration of the emission
- Avoid degradation of the semiochemicals
- Not produce contaminating residues
- Be economical and allow easy application of the semiochemical Although there is a large variety of emitting supports on the market such as rubber septa (Aldrich Co., UK; The West Co., Pennsylvania; Arthur H. Thomas Co.; Maavit Products, Tel Aviv, Israel), polyethylene pipes (Shin Etsu Chemical Co., Tokyo, Japan), porous plastic laminates (Hercon Lab. Co., New Jersey, USA); capillary fibers (Albany International, Massachusetts, USA), microcapsules (ICI Agrochemicals, Berks, UK), none of these emitting supports comply with all the above mentioned requirements.

Therefore, there is still the need of emitters of semiochemical substances with supports that acceptably satisfy said requirements and, precisely, this has been the purpose that the applicant's scientific research has sought. This research has allowed the attainment of the present invention.

DETAILED DESCRIPTION OF THE INVENTION

Just as it is stated in its title, the present invention refers to new emitters of semiochemical substances with a controlled emitting speed, to a process for the preparation thereof and to the applications thereof for the control of insect plagues in agriculture.

The emitters of the present invention, that comprise a support and a semiochemical substance adsorbed in the support, are characterized in that said support is a sepiolite and in that the retaining capacity between said sepiolite and said semiochemical substance is regulated in such a way that a controlled emission kinetics of said semiochemical substance is obtained.

Natural sepiolites are crystalline magnesium silicates. Structurally, they are formed in laminae of silica tetrahedrons connected by $Mg^{2+}$ cations, in octahedral coordination (see FIG. 1). The laminae form fibers of a length between 0.5 and 1.5$\mu$ and in turn, the fibers are connected together by means of Si—O—Si bridges and carbonates, forming beams with a thickness of about 200 Å

The specific surface of natural sepiolite is around 200–300 $m^2/g$, and can be modified to values between 80 and 600 $m^2/g$ (according to the B.E.T. method) by means of adequate treatments, wherein the Si—O—Si bridges are broken.

The size of the channel of natural sepiolite is relatively small and there is a high polarity inside it, caused by the water from crystallization and the end hydroxyl groups.

Due to this, the regular molecules of semiochemicals have difficulties in entering inside the channels, due to the size thereof and the lack of polarity, and consequently, the adsorption to the sepiolite support is superficial, in most of the cases.

The retaining capacity between the sepiolite and the semiochemical can be carried out from two aspects:

1.—Modification of the sepiolite
2.—Modification of the degree of compacting between the sepiolite and the adsorbed semiochemical.

Within the first group of modifications the following ones can be mentioned:

Modification of the surface cations of the sepiolite
Modification of the specific surface of the sepiolite Within the second group of modifications the following ones can be mentioned:

Modification of the compacting pressure
Modification of the surface/weight ratio of the finally obtained form Each one of these modifications will now be analyzed in a more detailed manner.

1. The modification of the surface cations of the sepiolite allows modification of the number of adsorption centers and the retaining force of the semiochemical on the part of the same. An illustrative example of this fact is constituted by the use of different sepiolites modified superficially wherein a specific percentage of surface octahedral magnesium has been replaced by mono or bivalent cations of groups IA and IIA or by protons. The modification of the surface cations of the sepiolite can be done by treatment of the natural sepiolite with acids (for example, sulfuric acid) or with bases (for example, sodium hydroxide).

2. The modification of the specific surface of the sepiolite is especially interesting, taking into account that the fixation of the molecules of semiochemical molecules to the first adsorption layer is much greater than the fixation that is produced in the second and successive layers. Upon increasing the adsorption surface of the sepiolite support, an increase of retention of the semiochemical is produced.

The modification of the specific surface is carried out by means of treatments similar to those indicated in item one above. Specific surface values between 80 and 600 $m^2/g$ can be achieved.

3. The modification of the compacting pressure during the manufacturing of the emitter makes it possible to act on the emitting speed. Hence, the greater the pressure at which the sepiolite is compacted with the semiochemical the greater the retention thereof on the support is, thus reducing the emitting speed. On the contrary, a compacting of both products at a lower pressure increases the emitting speed of the semiochemical. The range of compacting pressures is preferably between 0.1 and 20 $T/cm^2$, the pressure being chosen in terms of the needs of emission of the active substance.
4. The modification of the surface/weight ratio of the finally obtained emitting product also makes it possible to act on the emitting speed of the semiochemical. Hence, upon increasing the surface/weight ratio the emitting speed increases; on the contrary, upon reducing said ratio, the emitting speed reduces.

In accordance with the above, for the preparation of the emitters of the present invention one or several gradual modifications of the different physico-chemical variables mentioned in the above paragraphs can be made in order to adapt the sepiolite supports to the characteristics of the semiochemicals and to the specific needs of each emission kinetics for the treatment sought.

The emitters of the present invention can be prepared by associating the support and the semiochemical substance by conventional techniques such as agglomeration, pressing, drying by pulverization and the like, where binding components may or may not be used.

For example, the sepiolitic material can be impregnated, by adding to said powdered material a solution of semiochemical substance, trimedlure, in dichloromethane in a proportion of 1–20 ml of dichloromethane per gram of sepiolite+trimedlure, subsequently eliminating the dichloromethane.

The emitter thus obtained may be applied in the form of powder, wettable powder, granulate, pastilles, or conglomerates with any geometric shape that is desired. Likewise, they may be applied manually or by using any conventional mechanical device.

Preferably, the proportion of semiochemical substance/sepiolite is between 1 and 800 mg. Of semiochemical substance per gram of sepiolite, the proportion being chosen in terms of the needs of emission.

The emitters of semiochemical substances of the present invention are especially useful in order to treat insect plagues in the agricultural sector, either by population control techniques, massive captures, sexual confusion or any other type of attracticide traps, producing sterilizing actions in the insects, insecticides or hormone production inhibitors, among others.

In accordance with the above, the present invention provides new emitters of semiochemical substances that permit controlled and durable emission of the semiochemicals used in the environmental fight against agricultural plagues, with noteworthy advantages in comparison to the emitters developed up to now. Among said advantages the following ones can be emphasized:

The adaptation to the emitting needs and to the properties of each semiochemical.

The capacity to attain high useful life times

The non-existent pollution that they produce, since due to their chemical nature, they blend in the agricultural soil Their ease of application since they can be used in pastille, granulate or powder form.

The possibility of compacting them with different shapes in order to adapt them to any support.

BRIEF DESCRIPTION OF THE FIGURES

FIG. 1 It is a graph of the chemical structure of natural sepiolite, the different types of atoms are represented with the following symbols:

Silicon: •

Magnesium: ▽

Oxygen:○

Hydroxyl • inside a circle

Crystallization water: ⊕

FIG. 2 It is a graph of the influence of the cation on the trimedlure emission kinetics in accordance with Example 1.

The different sepiolites are represented win this figure with the following symbols:
  sep Na Mg 25%: ▲
  sep Mg: X
  sep H Mg 25%: ■

Figure 3:
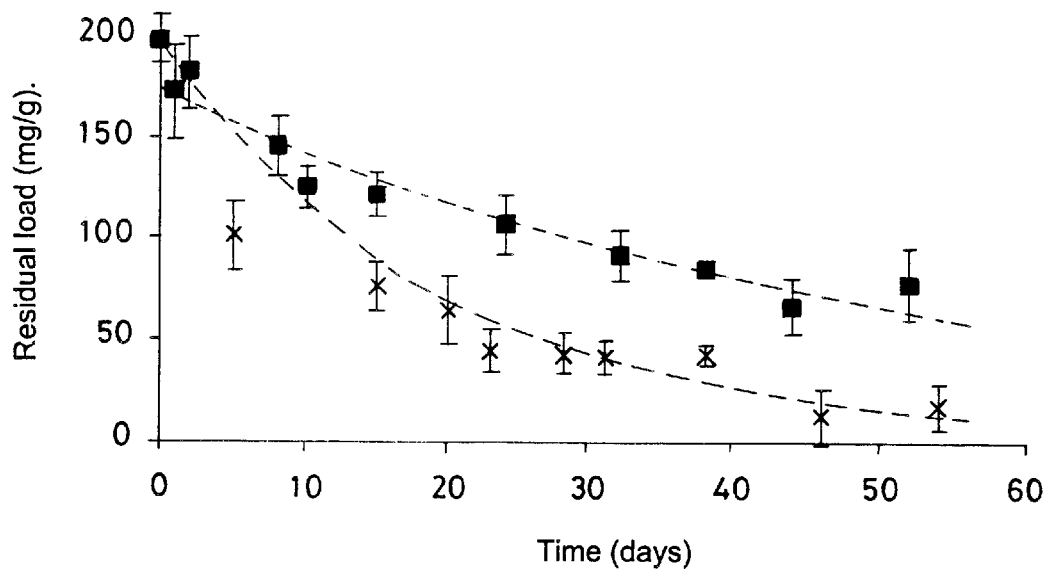

FIG. 3 It is a graph of the influence of the adsorption layer on the trimedlure emission kinetics in accordance with Example 2. The different sepiolites have been represented in this figure with the following symbols:
  sep H, $2^{nd}$. layer, 13%: ■
  sep H Mg 25%, $2^{nd}$. layer 33%: X FIG. 4 It is a graph of the influence of the compacting pressure on the trimedlure emission kinetics in accordance with Example 3. The different pressures are represented in the figure with the following symbols:
  Pressure 3.1 T/cm$^2$: ■
  Pressure 10.2 T/cm$^2$: ♦

Figure 5:
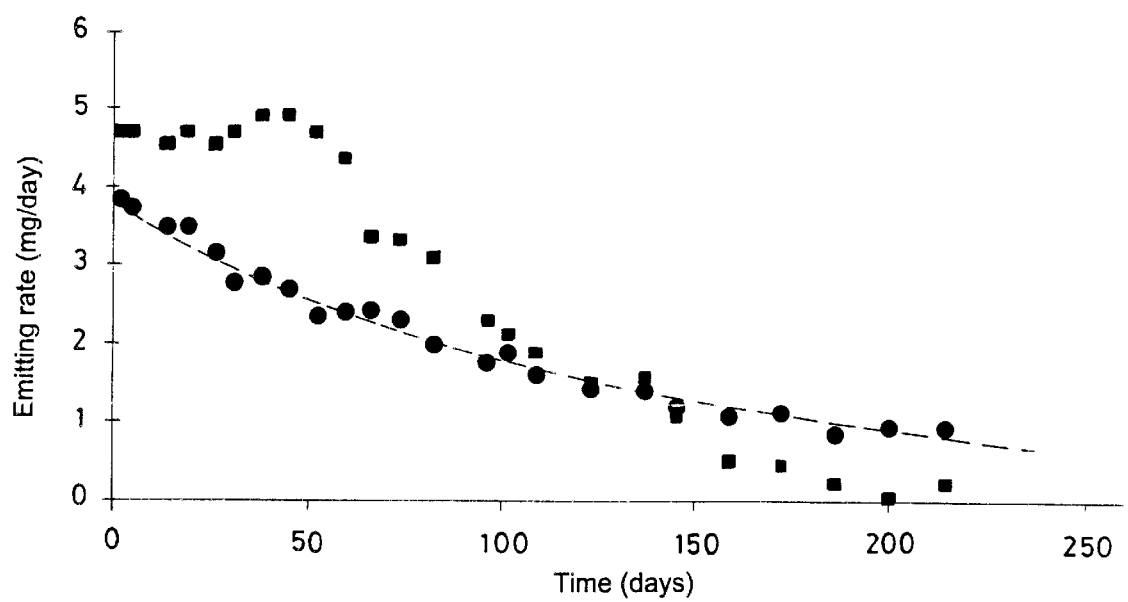

FIG. 5 It is a comparative graph of the field kinetics of a sepiolite in accordance with the invention in contrast to a conventional emitter according to Example 5. The sepiolite Na Mg has been represented by • and the can by ■ in this figure.

EMBODIMENTS OF THE INVENTION

Hereinafter several examples are given of the use of sepiolites and modified sepiolite materials, as a semiochemical support, and the adaptation thereof to predetermined emission kinetics, taking as the standard semiochemical trimedlure (tert-butyl 4-chloro-2-methylcyclohexane-1-carboxylate, attractant of fruit fly, *Ceratitis capitata*)

The emission kinetics of the trimedlure adsorbed in the different sepiolitic supports obtained is determined according to the following method:

1.—Impregnation of the sepiolite:

This is done by adding to the powdered sepiolitic material, a solution of trimedlure in dichloromethane and intense stirring for 1 hour, subsequently eliminating the dichloromethane. The impregnated sepiolitic material is homogenized by stirring for half an hour and then it is compacted in a press forming pastilles.

2.—Aeration and aging:

The pastilles are kept at 25° C. and with controlled aeration for 45 days. Periodically the amount of trimedlure that remains in the pastilles is determined, by means of extraction with soxhlet with the suitable solvent and qualitative gas chromatography. The emitting curves are drawn and the corresponding kinetics are determined with the obtained data.

The determination of the punctual emitting speed is done by using a thermostatted aerator, inside of which the pastille of sepiolitic material impregnated with trimedlure is placed periodically. A controlled air flow is circulated, with a constant temperature for a specific amount of time. When it comes out, the air passes through a cartridge of adsorbent, generally, a Sep-pak C18, where the trimedlure (TML) is retained. Subsequently the cartridge is removed and the amount of trimedlure emitted for a measured amount of time is determined by quantitative gas-liquid chromatography.

Example 1

Modification of the Surface Cations in Sepiolites for Controlled Emission of the Semiochemical Trimedlure Compared Emitting Supports:
  Sepiolite Mg (Natural)
  Sepiolite H Mg, 25% H$^+$. The octahedral Mg has been partially exchanged by H$^+$
  Sepiolite Na Mg, 25% Na$^+$. The octahedral Mg has been partially exchanged by Na.

Preparation of Sepiolites with Suitable Cations:

Sepiolite H Mg 25% was obtained from natural sepiolite by means of treatment with 1.3N H$_2$SO$_4$, at 50° C., for 30 min. with subsequent filtering and washing with water. The crystallinity of the sample is confirmed by X-ray diffraction.

Sepiolite Na Mg 25% was obtained by means of treatment of natural sepiolite with 1N NaOH, at room temperature, for 15 minutes and treatment in an autoclave at 200° C. for 6 hours, with subsequent filtering and washing. The crystallinity of the sample (70%) is determined by means of X-ray diffraction.

Figure 2:
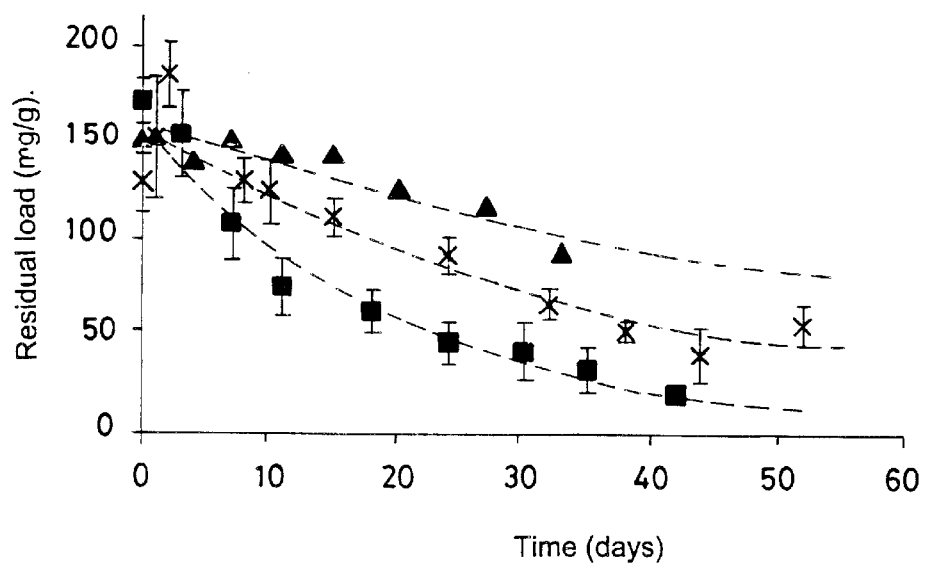

The kinetics obtained are shown in FIG. 2:(Influence of the cation on the emission kinetics). The maximum retention (most favorable emission kinetics) is obtained when the exchange cation is Na$^+$. The sepiolite H Mg retains less trimedlure than sepiolite Mg. The test is carried out with an initial load of 140 mg of trimedlure/g of sepiolite and pastilles with a 5 mm Ø, a weight of 0.09 g and compacted with a pressure of 10.2 T/cm$^2$.

Example 2

Modification of the Adsorption Layer for Controlled Emission of Trimedlure

For the amount of trimedlure given and using sepiolites with a different specific surface, the emitting speed thereof can be controlled, in terms of the percentage of trimedlure adsorbed in the 1$^{st}$. or in the 2$^{nd}$. adsorption layer. 420 mg of TML/g of sepiolite are used as the initial load.

Compared Emitting Supports:
  Sepiolite H Mg 25% in H$^+$. Specific surface 400 m$^2$/g. Percentage of TML in the 2$^{nd}$. layer: 33%
  Sepiolite H. Specific surface 520 m$^2$/g. Percentage of TML in the 2$^{nd}$. layer: 13%

Preparation of Sepiolites with the Adequate Surface:

Sepiolite H Mg 25% in H is prepared according to the method of the above example. Sepiolite H is prepared like sepiolite H Mg 25% but using 3N H$_2$SO$_4$.

The kinetics obtained are shown in FIG. 3: (Influence of the adsorption layer on the emission kinetics) The increase of retention is observed the larger the adsorption surface is and, therefore, the smaller the percentage of trimedlure absorbed on the second layer. The test is carried out with an initial load of 420 mg of trimedlure/g of sepiolite and pastilles with a 5 mm Ø, a weight of 0.09 g. In this way, by varying the proportion of semiochemical in the 1$^{st}$. and 2$^{nd}$. layer, the emission kinetics can be regulated.

Example 3

Modification of the Compacting Pressure of Sepiolites for Controlled Emission of the Semiochemical Trimedlure Emitting Supports:
  Sepiolite H Mg 25% impregnated with 140 mg of trimedlure and compacted at pressures of 3.1 and 10.2 T/cm$^2$. This sepiolite is described in example 1.

Figure 4:
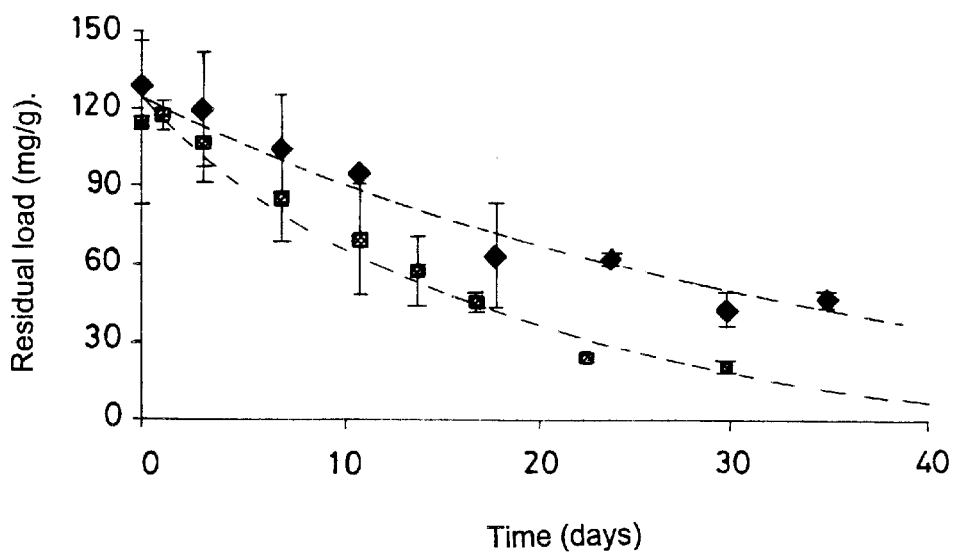

The kinetics obtained are shown in FIG. 4: (Influence of the compacting pressure on the emission kinetics). The increase of retention is observed when the compacting pressure increases. The test is carried out with an initial load of 140 mg of trimedlure/g of sepiolite and pastilles with a 5 mm Ø and a weight a 0.09 g. The verification that the kinetics obtained with the sepiolites are adequate and of long duration is observed in the following example.

Example 4

Comparison of the Effectiveness (Number of Captures and Useful Life Time of the Emitter), in the Emission of Trimedlure, of a Modified Sepiolite in Contrast to the Traditional Emitter Perforated Container Compared Emitting Supports:

Sepiolite Na Mg 25%, described above is used. The usual plastic can is used as a reference.

Method of Application:

The sepiolite is loaded with trimedlure and tablets are formed with a pressure of 2 T/cm². The initial load of the sepiolite pastilles is 500 mg of trimedlure, the pastilles are of 2.9 g; the container is also loaded with 500 mg. Yellow delta traps with an exchangeable floor impregnated with glue are used. The traps are placed in alternating trees (10 m of distance between the traps). Periodically captures are counted and the emitters are collected in order to analyze them in the laboratory by means of extraction and quantitative gas-liquid chromatography.

The emission kinetics of the compared systems are shown in FIG. 5: (Comparison of the field kinetics in sepiolites Na Mg 25% in comparison to the perforated can with the trimedlure emission). The most favorable kinetics is observed of the sepiolite Na that captures more flies and that keeps the activity for a longer period of time. A useful life time (period of effectiveness) of 185 days is obtained for sepiolite Na. The container is clearly inferior, with a useful life of 132 days.

What is claimed is:

1. A material for emitting semiochemical substances comprising
   a support and a semiochemical substance adsorbed in said support, wherein
   said support is a modified sepiolite having a retaining capacity for retaining said semiochemical substance, said retaining capacity of the modified sepiolite being adjusted in such a way that a controlled emission kinetics of said semiochemical substance is obtained,
   said modified sepiolite being at least one of
   a substituted sepiolite in which up to 40% of surface octahedral magnesium cations has been substituted by cations selected from metal cations of Group IA and IIA and protons;
   a surface-modified sepiolite having a specific surface value between 80 and 600 m²/g, said specific surface having been obtained by a treatment of the sepiolite selected from the group of treatments with an acid and treatments with a base;
   a compacted sepiolite having a degree of compaction and which has been compacted together with said semiochemical substance according to a compacting pressure between 0.1 and 20t/cm²;
   a surface/weight-modified sepiolite in which a selected surface/weight ratio has been adjusted;
   a plurally-modified sepiolite having properties of at least two of said substituted sepiolite, said surface-modified sepiolite, said compacted sepiolite and said surface-weight-modified sepiolite.

2. A material according to claim 1, wherein said substituted sepiolite has been prepared by treating natural sepiolite with a base.

3. A material according to claim 1, wherein said substituted sepiolite has been prepared by treating natural sepiolite with an acid.

4. A material according to claim 1, wherein said substituted sepiolite has been prepared by treating natural sepiolite with sulfuric acid.

5. A material according to claim 1, wherein said substituted sepiolite has been prepared by treating natural sepiolite with sodium hydroxide.

6. A material according to claim 1, wherein the surface/weight ratio and the degree of compactation of the support have been adjusted by compacting.

7. A material according to claim 1, wherein the surface/weight ratio of the surface-weight modified sepiolite has been adjusted during preparation of the support.

8. A material according to claim 1, comprising 1–800 mg of the semiochemical substance per gram of the support.

9. A material according to claim 1, wherein the semiochemical substance is impregnated in the support.

10. A material according to claim 1, wherein the semiochemical substance is trimedlure.

11. A material according to claim 1, wherein the material is a powder.

12. A material according to claim 1, wherein the material is a granulate.

13. A material according to claim 1, wherein the material is a tablet.

14. A process for manufacturing the material of claim 1, said process comprising the operations of modifying a sepiolite to provide a sepiolite support in which a semiochemical substance is adsorbed, in such a way that the retaining capacity of the sepiolite support permits a controlled release kinetics of said semiochemical substance, wherein the sepiolite is treated by at least one of
   substituting up to 40% of surface octahedral magnesium cations of the sepiolite by cations selected from metal cations of Group IA and IIA and protons, and adsorbing the semiochemical substance into the support;
   adjusting the specific surface of the sepiolite by a treatment selected from the group selected from treatments with an acid and treatment with a base, to obtain a specific surface value between 80 and 600 m²/g, and adsorbing the semiochemical substance into the support;
   compacting the sepiolite together with said semiochemical substance by applying a compacting pressure between 0.1 and 20t/cm²; and
   adjusting the surface/weight ratio has to a selected value surface/weight ratio value, and adsorbing the semiochemical substance into the support.

15. A process according to claim 14, wherein said surface magnesium cations are substituted by treating natural sepiolite with a base.

16. A process according to claim 14, wherein said surface magnesium cations are substituted by treating natural sepiolite with an acid.

17. A process according to claim 14, wherein said surface magnesium cations are substituted by treating natural sepiolite with sulfuric acid.

18. A process according to claim 14, wherein that said surface magnesium cations are substituted by treating natural sepiolite with sodium hydroxide.

19. A material according to claim 1, wherein said surface-modified sepiolite has been prepared by treating natural sepiolite with a base.

20. A material according to claim 1, wherein said surface-modified sepiolite has been prepared by treating natural sepiolite with an acid.

21. A material according to claim 1, wherein said surface-modified sepiolite has been prepared by treating natural sepiolite with sulfuric acid.

22. A material according to claim 1, wherein said surface-modified sepiolite has been prepared by treating natural sepiolite with sodium hydroxide.

* * * * *